United States Patent [19]

Wright et al.

[11] Patent Number: 5,516,486
[45] Date of Patent: May 14, 1996

[54] PROCESS FOR DISINFECTING COIR PLANT GROWTH MEDIA

[75] Inventors: Christopher T. Wright, Kingswood; Robert A. Simms, Woolston, both of United Kingdom

[73] Assignee: Solvay Interox Limited, Warrington, England

[21] Appl. No.: 302,746

[22] PCT Filed: Mar. 10, 1993

[86] PCT No.: PCT/GB93/00496

§ 371 Date: Nov. 15, 1994

§ 102(e) Date: Nov. 15, 1994

[87] PCT Pub. No.: WO93/18799

PCT Pub. Date: Sep. 30, 1993

[30] Foreign Application Priority Data

Mar. 14, 1992 [GB] United Kingdom .................. 9205600

[51] Int. Cl.⁶ ................ A61L 2/18; C05F 11/02
[52] U.S. Cl. ..................... 422/28; 422/1; 71/24
[58] Field of Search ................ 422/28, 34; 28/100, 28/165, 166, 167; 19/66 R; 71/24

[56] References Cited

U.S. PATENT DOCUMENTS

| 4,906,273 | 3/1990 | Wright | 71/9 |
| 5,000,874 | 3/1991 | Wiedemann | 252/400.22 |
| 5,300,127 | 4/1994 | Williams | 47/57.6 |

FOREIGN PATENT DOCUMENTS

| 0361955 | 4/1990 | European Pat. Off. . |
| 2139609 | 11/1984 | United Kingdom . |

OTHER PUBLICATIONS

Grant, *Hackh's Chemical Dictionary*, p. 498, 1969.

*Primary Examiner*—Robert J. Warden
*Assistant Examiner*—Theresa T. Snider
*Attorney, Agent, or Firm*—Larson and Taylor

[57] ABSTRACT

A method for disinfecting non-peat based plant-growth media, especially coir, which does not leave phytotoxic residues in the medium by contacting the medium with one or more water-soluble peroxygens is disclosed. The water-soluble peroxygen is preferably selected from the group comprising hydrogen peroxide and organic peracids, especially peracetic acid.

7 Claims, No Drawings

PROCESS FOR DISINFECTING COIR PLANT GROWTH MEDIA

FIELD OF THE INVENTION

This invention concerns a method for disinfecting. More specifically, the invention concerns a method for disinfecting peat-substitute growth media. Still more specifically, the invention concerns a method for disinfecting coir.

BACKGROUND OF THE INVENTION

The use of peat as a growth medium for plants has been a mainstay of British horticulture for many years. However, the extraction of peat from peat bogs has come under increasing pressure from environmental groups who are concerned for the loss of these ecosystems. This has lead to a search for alternative growth media which is more environmentally acceptable. One alternative is to use coir, a waste by-product from the processing of coconuts which has hitherto been stored in large waste dumps in regions where coconuts are processed, eg. Sri Lanka.

Coir is compacted into bricks to reduce its volume for transport. The bricks are then disintegrated to the constituent dust by use of an appropriate mill. The coir at this stage often contains about 15% by weight of water. Before sale as a plant growth medium, the coir is usually hydrated to about 70% by contacting the coir with water. 90% of the total hydration occurs within a few minutes of contact with the water, the hydration being completed while the coir is stored for approximately 24 hours. The fully hydrated coir is then available for sale.

As the coir in the dumps has usually been stored in the open in tropical climates for a long time, often for many years, there is a danger that the coir may be contaminated by, for example, fecal matter which may contain harmful microorganisms, especially coliform bacteria. These microorganisms are potentially harmful both to plants grown in the coir and also to those handling the material, especially where there is intimate contact between the material and eg. the hands of a user as would be the case in normal gardening and horticultural activities. It is therefore expedient that the coir is disinfected to ameliorate these risks.

However, many common disinfectants when employed at effective concentrations leave residuals or toxic by-products in a growth medium such as coir which are phytotoxic to seeds or plants, for example methyl bromide or active chlorine compounds. Accordingly, it is an object of the present invention to provide a method for disinfecting coir.

It is a further object of the present invention to provide a method for disinfecting coir which ameliorates or eliminates the disadvantages of alternative disinfectants for coir that is intended as a plant growth medium.

BRIEF SUMMARY OF THE INVENTION

According to the present invention, there is provided a method for disinfecting coir, characterized in that it comprises contacting the coir with a composition comprising one or more water-soluble peroxygens.

DESCRIPTION OF THE PREFERRED EMBODIMENT

According to a particular aspect of the present invention, there is provided a method for disinfecting coir, characterized in that it comprises contacting the coir with a composition comprising one or more water-soluble peroxygens in an amount that is sufficient to substantially disinfect the coir without leaving a phytotoxic residue therein, thereby enabling the disinfected coir to be used as a plant growth medium.

According to the method of the present invention, the coir may be contacted with the water-soluble peroxygen compound at any point during the processing of the coir to a finished plant growth medium. The contact may take the form of exposing the coir to the peroxygen as a vapor, but in many preferred embodiments, the coir is contacted with an aqueous solution of the peroxygen. In a particularly preferred embodiment the peroxygen is incorporated in the water used to hydrate the coir. Where this method is utilized, the water may be at any temperature from about 5° C. up to about 100° C., but in many embodiments, it is preferable that the coir is contacted with water at ambient temperatures, which are often from about 10° C. to about 30° C.

The water-soluble peroxygen may be introduced at a wide range of concentrations depending on the chosen water-soluble peroxygen and on the temperature at which it is applied. Typically, the concentration of the water-soluble peroxygen is selected from within a range from about 0.001% to about 5% by weight, preferably from about 0.005% to about 1% by weight, and more preferably from about 0.01% to about 0.5% by weight.

The water-soluble peroxygen may be any water-soluble peroxygen which has a disinfectant effect on the microorganisms present in the coir. In many embodiments, the water-soluble peroxygen is selected from the group comprising organic peracids and hydrogen peroxide. In particularly preferred embodiments, the water soluble peroxygen comprises an equilibrium mixture of an organic peracid, particularly an aliphatic peracid containing from 1 to 6 carbon atoms, hydrogen peroxide and the corresponding organic acid. In most preferred embodiments, the peracid is peracetic acid and the organic acid is acetic acid.

The water-soluble peroxygen may, for convenience, be supplied in a concentrated form to be diluted, for example with the hydration water, to the desired use concentration prior to or during contact with the coir. In many cases, the concentrate will contain up to about 45%, often from about 5% to about 30%, by weight of water-soluble peroxygens. In a particularly preferred embodiment, the peroxygen concentrate comprises by weight from 4.5 to 5.5% peracetic acid, 18 to 22% hydrogen peroxide and 9 to 14% acetic acid. The concentrate may optionally comprise stabilisers to prolong the storage stability of the peroxygen.

It has been found that when a water-soluble peroxygen compound is used to disinfect the coir, the peroxygen compound is decomposed relatively quickly by the coir, especially in the case of aliphatic peracids, but still gives excellent disinfection. This is particularly advantageous as the process does not leave a peroxygen residual which is phytotoxic. Moreover, in at least some embodiments, a treatment according to the present invention can promote germination and/or plant/seedling development in comparison with hydration of the coir with plain water.

Use of the hydration water to dilute the water soluble peroxygen is particularly advantageous as it reduces processing times and costs by effecting disinfection and hydration in a single operation.

Having described the invention in general terms, embodiments of the invention will now be described more fully by way of example only.

Disinfection of Coir

Six 50 gram samples of Sri Lankan coir containing 15% moisture were each gently stirred in a food blender. Each sample was inoculated with 10 mls of an aqueous solution containing approximately $10^5$ colony forming units per ml (cfu/ml) of *Escherichia coli* (*E. coil*) added over 1 minute with continued stirring to simulate a heavily contaminated material. To this mixture was added over 2 minutes, with continued stirring, 82 mls of the solution detailed in Table 1 below to give 70% hydration. All of the samples were allowed a 15 minute contact time, and then 190 mls of maximal recovery diluent plus 10 mls of 2.5 g/l catalase neutraliser were added to each sample. The samples were then plated out onto both violet red bile glucose agar (to determine the numbers of enterobacteriacae) and rose bengal chloramphenicol agar (to determine the numbers of yeasts/moulds). The violet red bile glucose agar samples were incubated for 24 hours at 37° C., and the rose bengal chloramphenicol agar samples were incubated for 5 days at 22° C. On completion of the incubation period, the numbers of colonies formed on the agars were counted, and the results for solutions E2 to E6 calculated as log reductions (LRF) in the numbers of colony forming units compared to the control C1. The results are given in Table 1 below.

The peracetic acid solution used in the Examples was an aqueous peracetic acid solution containing approximately 5% peracetic acid, 20% hydrogen peroxide and 12% acetic acid. The PAA soln % w/w in Table 1 refers to the concentration of the solution, not the active component.

TABLE 1

Results of Disinfection Trial

| Sample | PAA soln % w/w | Enterobacteriacae cfu/g | LRF | Yeasts/Moulds cfu/g | LRF |
|---|---|---|---|---|---|
| C1 | 0 | 5800 | — | $9.4 \times 10^5$ | — |
| E2 | 0.1 | 1200 | 0.7 | $9.7 \times 10^4$ | 1.0 |
| E3 | 0.25 | 82 | 1.8 | $7.4 \times 10^4$ | 1.1 |
| E4 | 0.5 | 14 | 2.6 | $2.6 \times 10^4$ | 1.6 |
| E5 | 1.0 | <5 | >3.8 | $1.1 \times 10^4$ | 1.9 |
| E6 | 2.0 | <5 | >3.8 | $3.4 \times 10^3$ | 2.4 |

The results show that peracetic acid gave excellent reductions in the numbers of colony forming units in the coir. Even in Example E2 at a dose rate of 0.1% of a 5% solution, a greater than fourfold reduction in Enterobacteriacae was achieved. In Example E5, a 1% dose of a 5% solution gave a substantially complete kill of Enterobacteriacae. An additional benefit of the use of a peroxygen disinfectant was that the yeasts and moulds which are found naturally in the coir were significantly reduced in number, for example, in Example E6, a dose of 2% of a 5% peracetic acid solution resulted in a greater than three hundredfold reduction in yeast/mould colony forming unit numbers.

Persistence of Peracetic Acid

The samples 1 to 6 from the disinfection trial were analysed for the presence of peracetic using a test strip commercially available from Merck at regular intervals, and the time in minutes for the peracetic acid to decompose recorded. The results are given in Table 2 below.

TABLE 2

Results of Peracetic Acid Persistence Trial

| Sample | Time for Peracetic Acid to Decompose (Minutes) |
|---|---|
| E2 | 5 |
| E3 | 6 |
| E4 | 7 |
| E5 | 10 |
| E6 | 14 |

The results given in Table 2 show that the peracetic acid levels were reduced rapidly during the disinfection period, and, for example in Example E6, a 2% dose of a 5% peracetic acid solution left no detectable peracetic acid residue in the coir after only 14 minutes.

We claim:

1. A method for disinfecting coir, said method comprising contacting coir intended for use as a plant growth media with a composition comprising an aqueous solution of a $C_1$ to $C_6$ aliphatic peracid, in an amount that is sufficient to substantially disinfect the coir without leaving a phytotoxic residue therein, thereby enabling the disinfected coir to be used as a plant growth medium.

2. A method according to claim 1, wherein the aqueous solution hydrates the coir.

3. A method according to claim 1 or 2, wherein the $C_1$ to $C_6$ aliphatic peracid is incorporated into the aqueous solution at a concentration selected in the range from about 0.001% to about 5% by weight.

4. A method according to claim 3, wherein the $C_1$ to $C_6$ aliphatic peracid comprises from about 0.01% to about 0.5% by weight of the aqueous solution.

5. A method according to claim 1 or 2, wherein the aliphatic peracid comprises peracetic acid.

6. A method for disinfecting coir for use as a plant growth medium, said method comprising contacting coir intended for use as a plant growth media with a composition comprising from 0.01 to 0.5% by weight of peracetic acid until at least some disinfection has occurred.

7. Coir which is disinfected by a method according to claim 1.

* * * * *